United States Patent [19]

Resnick

[11] Patent Number: 4,571,739
[45] Date of Patent: Feb. 18, 1986

[54] INTERORAL ELECTROLARYNX

[76] Inventor: Joseph A. Resnick, Rd. #1, Box 415A, Natrona Heights, Pa. 15065

[21] Appl. No.: 533,002

[22] Filed: Sep. 16, 1983

Related U.S. Application Data

[63] Continuation-in-part of Ser. No. 319,039, Nov. 6, 1981.

[51] Int. Cl.[4] ............................................. A61F 1/20
[52] U.S. Cl. ...................................... 381/70; 433/167
[58] Field of Search ..................... 179/121 C, 107 BC; 381/70; 181/127; 433/32, 167, 202

[56] References Cited

U.S. PATENT DOCUMENTS

| | | | |
|---|---|---|---|
| 2,093,453 | 9/1937 | Kellotat | 179/1 AL |
| 2,161,169 | 6/1939 | Jefferis, Jr. | 433/167 X |
| 2,862,209 | 12/1958 | Cooper | 3/1.3 |
| 3,084,221 | 4/1963 | Cooper et al. | 179/1 AL |
| 3,914,550 | 10/1975 | Cardwell, Jr. | 179/1 AL |
| 4,473,905 | 9/1984 | Katz et al. | 381/70 |
| 4,502,151 | 2/1985 | Castle et al. | 381/70 |

FOREIGN PATENT DOCUMENTS

| | | | |
|---|---|---|---|
| 61702 | 10/1982 | European Pat. Off. | 3/1.3 |
| 1592872 | 7/1981 | United Kingdom | 179/1 AL |

OTHER PUBLICATIONS

Stern, Kenneth J., *A Self-Contained Intra-Oral Artificial Larynx*, Apr. 20, 1979.
Goode & Carroll, "An Intraoral RF Powered Artificial Larynx," Proceedings of 23rd Annual Conference on Engineering in Medicine and Biology; Washington, D.C., Nov. 16–19, 1970, p. 335.
Medorobics, Inc., Disclosure Circulated at International Association of Laryngeltomees Annual Convention, Witchita, Kansas, Summer 1982.

*Primary Examiner*—Keith E. George
*Attorney, Agent, or Firm*—Fay, Sharpe, Fagan, Minnich & McKee

[57] ABSTRACT

A prosthetic tone emitter for laryngectomy patients which in combination with natural apparatus enables comprehensible speech. Components of the tone emitter are constructed into an artificial tooth such that articulation is relatively unhindered.

4 Claims, 5 Drawing Figures

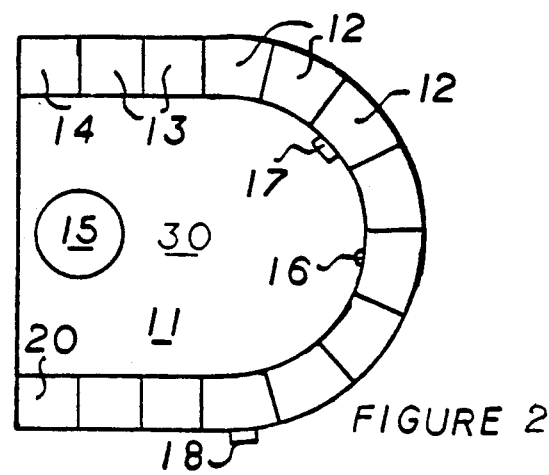
FIGURE 2
FIG 4
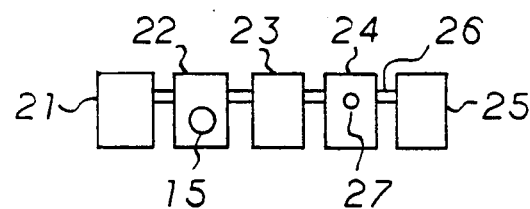

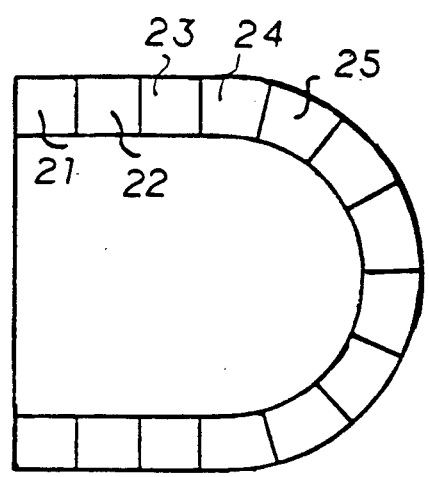

INTERORAL ELECTROLARYNX

PRIOR APPLICATION

This is a continuation-in-part of a copending application, Ser. No. 319,039 filed Nov. 6, 1981 entitled "Prosthetic Device For Artificial Speech".

BACKGROUND

This invention relates to the field of sound producing prosthetic devices for use by laryngectomized humans.

The human larynx functions to produce a tone which is modulated or otherwise acted upon by the teeth, tongue, lips, palate to produce speech. Persons who have had laryngectomy operations, or who have other laryngeal dysfunctions, are unable to speak naturally because they cannot produce the required tones.

Many devices have been developed for enabling artificial speech. The usual practice is to generate a tone within the oral cavity which can then be shaped into speech. Most such devices are located external to the oral cavity, but a few are partially inserted therein, and at least one device is entirely located within the oral cavity. This latter device is described in a European Patent Application No. (82102411.4) entitled "Artificial Larynx", European publication Ser. No. 0-061-702, filed Mar. 23, 1982, which has a U.S. application Ser. No. 249,140 filed Mar. 30, 1981 now U.S. Pat. No. 4,473,905, to Katz et al, this patent being incorporated herein by reference. The Katz device has a tone emitting circuit, battery, and speaker embedded within a flat plate which is held within the mouth like a dental plate.

The devices which are located within the oral cavity have several advantages over externally located devices, but also have the disadvantage of interference with the articulation needed to shape the tone into the sounds which are identified as speech. The physical presence of the device may prevent the lips and tongue from assuming the positions appropriate to specific sounds or words, or the device may reflect sound waves. The result is decreased quality.

Consequently it is desired to provide an improved electrolarynx with reduced interference with articulation.

SUMMARY OF THE INVENTION

The present invention incorporates major components of the electrolarynx into the interior of artificial teeth which are inserted into locations where the patient lacks a natural tooth. The entire device may be incorporated into artificial teeth if the patient has sufficient empty tooth locations or is willing to permit extraction of a number of natural teeth.

One embodiment comprises a replaceable battery containing artificial tooth; a fixed speaker containing artificial tooth; and a fixed circuit containing artificial tooth.

The artificial tooth, or teeth, added to the oral cavity of the user actually improves articulation by filling a gap where a natural tooth is missing.

BRIEF DESCRIPTION OF THE DRAWINGS

FIG. 2 is a diagrammatic plan view of a human oral cavity having an electrolarynx therein;

FIG. 3 is similar to FIG. 1 with all components of the electrolarynx located within three artificial teeth; and FIG. 4 is a profile view of artificial teeth containing an electrolarynx.

DETAILED DESCRIPTION

The invention is an oral cavity placed miniature sound emitter comprising an electrical circuit containing a power source, a speaker or speakers, and other electrical components needed to produce an audible tone. The circuit may be incorporated into an artificial tooth or teeth, or incorporated into a combination of a denture plate with artificial teeth.

For the purposes of the claims and this specification, an artificial tooth is defined as a structure having the approximate size and shape of a natural tooth and adapted in material strength and composition for substitution in an oral cavity for a natural tooth.

The emitter generates a tone which can be shaped by natural apparatus, e.g. tongue, lips, palate and teeth, to form the sounds identified as human speech. Location of the emitter in the oral cavity is of significant advantage: generation of the sound directly in the oral cavity rather than externally results in a reduction in sound which escapes formation into speech and exists in the vicinity of the user as superfluous, background noise. Such background noise not only detracts from the quality of artificial speech, but may also be a source of embarrassment. Location in the oral cavity reduces input power needed to produce normal speech intensity levels.

The emitter could contain taped or otherwise stored complete speech units to enable a preplanned, pretaped message.

Location of the tone emitter in the oral cavity conceals the device, a social and psychological advantage.

The tone emitter can have a variety of switching means for control (as example: magnetic reed switches, rocker dip switch). Switches may be provided to turn the power on and off, for selecting different sound intensities, and even for the selection of discrete tone frequencies. Additionally and/or alternatively, resistors and/or capacitors or other electrical components may be variable to control sound intensity and frequency over a range.

The electrical circuit may be tunable to a frequency approximately appropriate to the age and sex of the user, or such matching may be done by selection of an appropriately designed model.

Design and construction of a miniature electrical circuit to accomplish the above goals, is considered to be easily accomplished by persons of ordinary skill in the art. Albeit non-essential, in the following, a specific circuit embodiment will be disclosed.

MULTI-VIBRATOR ELECTRICAL CIRCUIT

Figure 1:
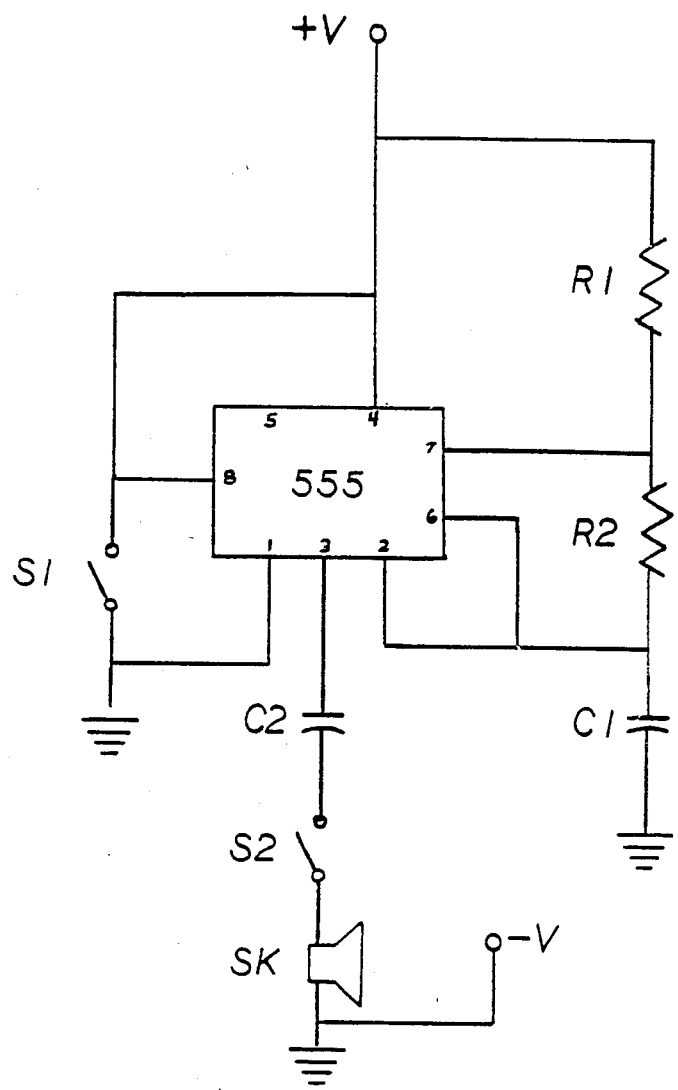
FIG. 1 is an electrical circuit diagram.

Refer to FIG. 1 which is a circuit diagram of one possible embodiment. The box labeled 555 is a number 555 integrated chip (a timer) which is a standard device. Table I supplies preferred parameters for electrical components.

TABLE I

| FIGURE 1 ELECTRICAL COMPONENTS | |
|---|---|
| C1 | .01 mf |
| C2 | 10 μf |
| R1 | 1000 ohms |
| R2 | 100K ohms |

TABLE I-continued

| FIGURE 1 ELECTRICAL COMPONENTS | |
|---|---|
| S1 | Rocker Dip Switch |
| S2 | Reed, or Proximity Switch |
| V | 1.5 to 30 VDC Battery Source |
| SK | Speaker |

Alternatively, the electrical circuits described by the prior art may be used. For example, FIGS. 2 and 3 of the incorporated Katz et al. reference teach a circuit which is described in detail in the specification.

MODES OF PLACEMENT IN ORAL CAVITY

Refer to FIGS. 2, 3 which show examples of placement modes. In FIG. 2 the emitter is constructed into a lower denture plate 11 which supports artificial teeth 12, of which three are so numbered: At least one artificial tooth, number 13, has constructed within most of the electrical components needed for the emitter. Tooth 14 may be a removable, replacable power source (battery) containing tooth. Speaker 15 emits the needed tone, and is shown located within plate 11, generally at the rear of the oral cavity. A plurality of speakers could be used, perhaps located in teeth 14 and 20. Necessary switches can be located in rear facing positions such as shown at 16 and 17, for activation by the tongue, or may be located in a forward facing position as at 18 for activation by a finger or hand held tool. Other electrical components such as resistors and capacitors, whose values may be varied, may be located to allow adjustment by replacement.

Interconnecting wires in the circuit may be embedded in plate 11.

The placement mode of FIG. 2 shows the use of denture plate. The emitter components are shown in FIG. 2 to be distributed in several artificial teeth which are supported by plate 11. This design would be appropriate to a user with many missing natural teeth. The size and thickness of plate 11 is reduced by incorporation of components within artificial teeth 12.

The optimum design is variable with the user but can be stated to be the incorporation of all components within a number of artificial teeth equal to or less than the number of missing teeth in the oral cavity of the user, with no denture plate used. The entire emitter would be within artificial teeth and the articulation of sound would be done with an essentially intact, unobstructed oral cavity, i.e., the device will not interfere with articulation.

Figure 5:
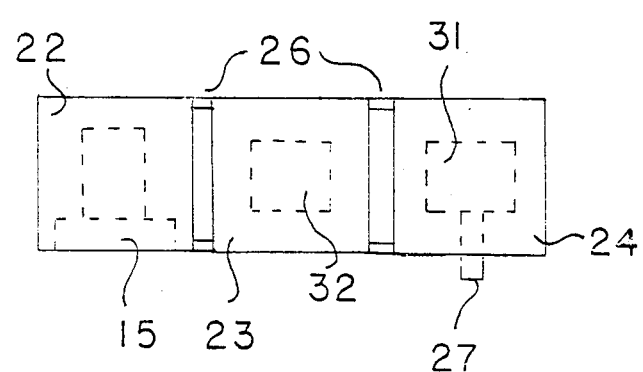
FIG. 5 is a plan view of artificial teeth containing an electrolarynx.

In FIG. 3, an emitter is illustrated which is appropriate to a user having 3 missing adjacent molars. No plate is used. Teeth 21 and 25 are natural teeth to which artificial teeth 22, 23, and 24 are attached. The means of attachment is well known to the art of dentistry, and is also described (dental wires) in the Katz et al reference. Artificial tooth 22 will contain a speaker, with the face of the speaker facing into the oral cavity and away from the cheek. Artificial tooth 23 is a removable tooth which contains a battery power supply for the circuit of the electrolarynx. The remaining components of the circuit, including at least one switch, is in artificial tooth 24. FIG. 4 shows a profile of the emitter in which natural teeth 21, 25 support artificial teeth 22, 23, and 24 via wires 26. Item 27 is a switch which controls the sound tone. Artificial tooth 22 contains speaker 15 and artificial tooth 23, a removable tooth, contains a battery. Electrical connections between the artificial teeth may be via wires 26, or precision prosthodontal appliances which support the appliance. FIG. 5 is a plan view of a similar arrangement as shown in FIG. 4.

An object of this invention is to provide a minimum of interference with articulation. Consequently, the embedding of components within artificial teeth should be such as to present a smooth tooth face on both sides of the tooth. On the bucaal, cheek side of the tooth, a smooth surface prevents sores. On the lingual, cavity side, a smooth surface optimizes articulation.

Speaker 15 must penetrate to the outer surface of artificial tooth 22 to increase sound transmission, but may be flush with the flat surface. In FIG. 3, no protrusion of speaker 15 beyond tooth 22 is shown.

The battery may be wholly encased within artificial tooth 23 with penetration to the surface of electrical connectors only. The entire artificial tooth 23 may be removed and replaced to enable recharging.

Switch 27 will protrude somewhat in to the oral cavity 30 but is only a small obstruction to articulation.

The elimination of a plate should reduce the occurrence of sores in the mouth of the user due to vibration rubbing.

The inclusion of a battery and a speaker within artificial teeth has been demonstrated in a bench mockup of a human oral cavity using commercially available components. A battery sold by Gould (Activair 2, 312 HP) is considered suitable as in a Knowles BK-1610 speaker.

I claim:

1. A tone emitter for the electrical generation of a sound tone for artificial speech which tone emitter is sufficiently small in size and adopted for placement entirely within a human oral cavity and which tone emitter has a first removable, artificial tooth which contains a battery power source and a second artificial tooth which contains a speaker.

2. The tone emitter of claim 1 wherein said speaker is substantially encased within said artificial tooth.

3. A sound emitter for the electrical generation of a sound tone sized for construction into an artificial component of the human oral cavity to produce artificial speech by the introduction of a tone directly into the oral cavity comprising:

a battery powered source contained within a first artificial tooth;

a speaker for tone emission contained within a second artificial tooth;

switch means for selectively operating said sound emitter; and, circuit means operatively associated with said power source, speaker and switch means whereby the sound emitter may selectively generate a sound tone for the production of artificial speech.

4. The sound emitter as claimed in claim 3 wherein said switch means is positioned for tongue actuation and includes a switch for turning the power source on and off.

* * * * *